(12) United States Patent
Fu et al.

(10) Patent No.: US 8,669,295 B2
(45) Date of Patent: Mar. 11, 2014

(54) PROCESS FOR PREPARING METHANOL, DIMETHYL ETHER, AND LOW CARBON OLEFINS FROM SYNGAS

(75) Inventors: Qiang Fu, Beijing (CN); Xiaoxin Zhang, Bejing (CN); Yibin Luo, Beijing (CN); Xuhong Mu, Beijing (CN); Baoning Zong, Beijing (CN)

(73) Assignees: China Petroleum & Chemical Corporation, Beijing (CN); Research Institute of Petroleum Processing, Sinopec, Beijing (CN)

( * ) Notice: Subject to any disclaimer, the term of this patent is extended or adjusted under 35 U.S.C. 154(b) by 430 days.

(21) Appl. No.: 13/131,028

(22) PCT Filed: Nov. 26, 2009

(86) PCT No.: PCT/CN2009/001325
§ 371 (c)(1),
(2), (4) Date: Jul. 8, 2011

(87) PCT Pub. No.: WO2010/060279
PCT Pub. Date: Jun. 3, 2010

(65) Prior Publication Data
US 2012/0115966 A1    May 10, 2012

(30) Foreign Application Priority Data
Nov. 28, 2008 (CN) .......................... 2008 1 0227830

(51) Int. Cl.
*C07C 27/00* (2006.01)
(52) U.S. Cl.
USPC ............ 518/714; 518/700; 518/713; 518/715
(58) Field of Classification Search
None
See application file for complete search history.

(56) References Cited

U.S. PATENT DOCUMENTS

| 4,349,464 A | 9/1982 | Wainwright et al. |
| 4,366,260 A | 12/1982 | Wainwright et al. |
| 4,436,833 A | 3/1984 | Broecker et al. |
| 5,389,689 A | 2/1995 | Fujimoto et al. |
| 2007/0244000 A1 * | 10/2007 | Molinier et al. .............. 502/300 |

FOREIGN PATENT DOCUMENTS

| CN | 1065026 A | 7/1992 |
| CN | 1073726 A | 6/1993 |
| CN | 1537674 A | 10/2004 |
| CN | 1683076 A | 10/2005 |
| CN | 101164692 A | 4/2008 |
| EP | 0266727 A | 5/1988 |
| JP | 58159847 A | 9/1983 |

OTHER PUBLICATIONS

Li Wang, Researching Progress for Catalyst of Methanol Synthesis, Chemical Fertilizer Design, Jun. 2003, vol. 45, No. 3, pp. 55-58.

* cited by examiner

*Primary Examiner* — Sudhakar Katakam
(74) *Attorney, Agent, or Firm* — Novick, Kim & Lee, PLLC; Allen Xue (57) ABSTRACT

The present invention provides a process for preparing methanol, dimethyl ether, and low carbon olefins from syngas, wherein the process comprises the step of contacting syngas with a catalyst under the conditions for converting the syngas into methanol, dimethyl ether, and low carbon olefins, characterized in that, the catalyst contains an amorphous alloy consisting of a first component Al and a second component, said second component being one or more elements or oxides thereof selected from Group IA, IIIA, IVA, VA, IB, IIB, IVB, VB, VIB, VIIB, VIII, and Lanthanide series of the Periodic Table of Elements, and said second component being different from the first component Al. According to the present process, the syngas can be converted into methanol, dimethyl ether, and low carbon olefins in a high CO conversion, a high selectivity of the target product, and high carbon availability.

20 Claims, 2 Drawing Sheets

Figure 1: XRD Spectra [(1) Example 1 catalyst, (2) Comparative Example 1 Catalyst, (3) Comparative Example 2 catalyst]

Figure 2: XRD Spectra [(1) Example 8 catalyst, (2) Example 9 catalyst]

Figure 3: XRD Spectrum of Comparative Example 4 catalyst

PROCESS FOR PREPARING METHANOL, DIMETHYL ETHER, AND LOW CARBON OLEFINS FROM SYNGAS

THE TECHNICAL FIELD

The present invention relates to a process for preparing methanol, dimethyl ether, and low carbon olefins from syngas.

BACKGROUND

The synthesis of methanol is an important chemical engineering process. Currently, the Cu—Zn—Al catalyst is the main component of the widely-used industrial catalyst for the synthesis of methanol at a low pressure. It is generally prepared by a co-precipitation method, and the resultant catalyst is a mixture of Cu, Zn, and Al oxides. For example, U.S. Pat. No. 4,436,833 discloses a co-precipitation method comprising mixing a solution of Cu, Zn, and Al nitrates with sodium carbonate as a precipitation agent to form a carbonate precipitate, washing off the sodium ions with distilled water, and drying and calcining to produce a mixture of Cu, Zn, and Al oxides for catalytic synthesis of methanol. The catalyst, however, has the disadvantage that it is difficult to wash off the sodium ions and control the temperature during the reduction process, resulting in a significant decrease of the catalytic activities.

U.S. Pat. No. 4,366,260 discloses a method for preparing methanol, or mixtures of methanol and dimethyl ether. The catalyst used in the method is a Raney Cu catalyst which is prepared from an alloy containing from 35 to 60% by weight of aluminum, 0.1 to 25% by weight of zinc, and the remainder being substantially all copper. It is known to those skilled in the art that the alloy of the Raney Cu catalyst is a crystalline alloy. The methanol yield by means of the catalyst under the reaction conditions suitable for preparing methanol from syngas is relative low (10.9% only).

Dimethyl ether (DME) is a widely interesting, environmentally friendly, super-clean replacement product for civilian and automobile fuels. There are mainly two production methods of dimethyl ether, i.e. one-step method and two-steps method. The two-steps method resides in synthesizing methanol from syngas, and then dehydrating to produce dimethyl ether. The one-step method means that dimethyl ether is synthesized from the feedstock syngas in one step, and comprises three main reaction steps which are relevant from each other and proceed sequentially:

$$CO + 2H_2 \rightarrow CH_3OH \qquad (1)$$

$$2CH_3OH \rightarrow CH_3OCH_3 + H_2O \qquad (2)$$

$$CO + H_2O \rightarrow CO_2 + H_2 \qquad (3)$$

Although all three reactions are reversible, the whole reaction procedure can proceed in a state which deviates from the thermodynamic equilibrium since products from each of the reaction step are consumed in the next reaction. Therefore, compared with a single methanol synthesis reaction, the conditions for the dimethyl ether synthesis reaction process directly from syngas are much milder, and the one-pass CO conversion is much higher. Compared with the two-steps method, the one-step method for dimethyl ether synthesis is carried out without an intermediate procedure for the methanol synthesis, and it has the advantages of simpler procedure, less devices, and lower investment and operation cost. Therefore, the production cost for dimethyl ether is decreased and the economic benefit is increased. Thus, the one-step method for dimethyl ether synthesis is of great interest in the research & development in many countries. The catalyst system for the one-step synthesis of dimethyl ether is generally a physical mixture of a methanol synthesis catalyst and a methanol dehydration catalyst. The industrial catalyst for methanol synthesis generally contains one or more of Cu, Zn, Al and Cr, and it is well known for those skilled in the art that the catalyst is a crystalline alloy, whereas the methanol dehydration catalyst is generally chosen from solid acidic materials.

U.S. Pat. No. 5,389,689 discloses a preparation method of the catalyst for producing dimethyl ether in one-step, comprising pulverizing the mixture containing zinc oxide, copper oxide or chromic oxide, and aluminum oxide to particle sizes of from about 0.1 to 20 μm, pressing under a pressure of 100-500 kg/cm$^3$ to adhere the oxides together, then suspending in the solvent and again pulverizing the slurry formed therefrom to obtain the catalyst. Under the reaction conditions comprising a $H_2$/CO molar ratio of 1, a reaction temperature of 280° C., and a reaction pressure of 3 MPa, the CO conversion is 60.1%, the yield of dimethyl ether is 42.8%, and the yield of $CO_2$ is 14.4%. The catalyst for producing dimethyl ether has a low activity, the temperature desired is relatively high, and the CO conversion is relatively low. Moreover, about one third of CO is converted into useless $CO_2$ due to the low hydrogenation activity of the catalyst. Other side reactions occur during the reaction procedure, resulting in carbon availability of generally less than 60%. The reaction process is less cost-effective.

Light olefins which mainly refer to ethylene and propylene are very important raw materials for the chemical engineering. Presently, more than 90% of light olefins are produced from the cracking of light oils. The supply of light olefins is unable to meet the demand in the market. In view of the economic continuous development, and increasing deficiency of the petroleum source, it is absolutely necessary to produce light olefins from a replacement source. The technique for directly preparing olefins from syngas originates from the traditional F-T synthesis. Since the carbon number of the product obtained from the F-T synthesis catalyst follows the S-T distribution law, the selectivity of low carbon olefins is low. The preparation of catalysts having a high activity and selectivity is of great interest in the current research field.

CN1065026A discloses a catalyst for preparing ethylene from syngas. The catalyst comprises one oxide of the element selected from Si, Al, Ti, Nb, and Hf, one or two oxides of the element selected from Nb, Y, Ga, Ge, In, and Tl, one or more oxides of the element selected from Sn, Pb, Sc, La, Pr, Ce, and Nd, and is prepared by a method selected from impregnation, co-precipitation, mechanical mixing, slurry-mixing, a combination of impregnation and co-precipitation, or a combination of mechanical mixing and impregnation. Although the ethylene selectivity can be up to 94% when the catalyst is used in the preparation of ethylene from syngas, the CO conversion is only 15%.

CN1537674A discloses a Fe/active carbon catalyst for the preparation of ethylene, propylene and butylene from syngas. The catalyst comprises α-Fe, FexCy, (Fe,Mn)O, CuO, ZnO, and $K_2O$, and its specific surface is 350-400 m$^2$/g. The catalyst for the preparation of low carbon olefins from sygnas is prepared by loading Fe onto the active carbon by a vacuum impregnation method, sufficiently dispersing Fe and adjutants onto the active carbon, and calcining the resultant at a temperature of 500-800° C. By use of the catalyst, the CO conversion at 300° C. is 97.3%, and the $C_2^=$-$C_4^=$ selectivity in the organic products is 43%. However, the contents of methane and ethane in the products are relatively high (15% and 12% respectively, based on the total organic products). Therefore, the carbon availability is low.

SUMMARY OF INVENTION

The present invention aims to overcome the disadvantages of low CO conversion, target product selectivity, and carbon availability during the prior preparation process of methanol, dimethyl ether and/or low carbon olefins from syngas, and to provide a preparation process of methanol, dimethyl ether and/or low carbon olefins from syngas which has a high CO conversion, target product selectivity, and carbon availability.

The present invention provides a process for preparing methanol, dimethyl ether, and light olefins from syngas, wherein the process comprises the step of contacting syngas with a catalyst under the conditions for converting the syngas into methanol, dimethyl ether, and low carbon olefins, characterized in that, the catalyst contains an amorphous alloy consisting of a first component Al and a second component excluding Al element, and said second component comprises one or more elements or oxides thereof selected from Group IA, IIIA, IVA, VA, IB, IIB, IVB, VB, VIIB, VIIB, and VIII, and Lanthanide series of the Periodic Table of Elements.

In the inventive process for preparing methanol, dimethyl ether, and low carbon olefins from syngas, the use of the catalyst containing an amorphous alloy consisting of a first component Al and a second component, said second component being one or more elements or oxides thereof selected from Group IA, IIIA, IVA, VA, IB, IIB, IVB, VB, VIIB, VIIB, and VIII, and Lanthanide series of the Periodic Table of Elements results in a very high CO conversion, target product selectivity, and carbon availability.

DETAILED DESCRIPTION OF THE EMBODIMENT

The term "syngas" (synthesis gas) means a feedstock gas mixture comprising CO and H2 as the main components. The syngas is generally obtained from solid raw materials (e.g. coal, coke), liquid raw materials (e.g. light oils, heavy oils), and gaseous raw materials (e.g. natural gases, oil field gases). For example, the syngas can be one or more gases selected from of coke oven gases, liquefied gases, water gases, semi-water gases, natural gases, and oil field gases.

The present invention provides a process for preparing methanol, dimethyl ether, and low carbon olefins from syngas, wherein the process comprises the step of contacting syngas with a catalyst under the conditions for converting the syngas into methanol, dimethyl ether, and low carbon olefins, characterized in that, the catalyst contains an amorphous alloy consisting of a first component Al and a second component, said second component being one or more elements or oxides thereof selected from Group IA, IIIA, IVA, VA, IB, IIB, IVB, VB, VIIB, VIIB, and VIII, and Lanthanide series of the Periodic Table of Elements, and said second component being different from the first component Al.

According to process provided by the present invention, preferably, based on the total weight of the amorphous alloy, the amount of Al is 0.5-60 wt. %, preferably 20-55 wt. %, and the amount of the second component is 40-99.5 wt. %, preferably 45-80 wt. %. On the other hand, if the preparation method of the amorphous alloy comprises an alkaline-washing step for Al, the amount of Al is preferably 0.5-20 wt. %, more preferably 5-15 wt. %, and the amount of the second component is preferably 80-99.5 wt. %, more preferably 85-95 wt. %.

According to process provided by the present invention, preferably, said second component is one or more elements or oxides thereof selected from Lanthanide series, and the third, fourth and fifth rows of Group IA, IIIA, IVA, VA, IB, IIB, IVB, VB, VIIB, VIIB, and VIII of the Periodic Table of Elements, more preferably one or more elements or oxides thereof selected from Cu, Zn, V, Cr, Mn, Fe, Co, Ni, K, Zr, Mo, Sn, C, Si, La, and P. In some embodiments, said second component comprises Cu or the oxide thereof. In some other embodiments, said second component comprises or consists of Cu and Zn or the oxides thereof. In some other embodiments in which the amorphous alloy contains Cu, the amount of the Group VIII element or the oxide thereof, if present, is less than 30 wt. %, preferably less than 20 wt. %, based on the total weight of the amorphous alloy. In some other embodiments in which the amorphous alloy contains Cu, the alloy can be free of the Group VIII element or oxide thereof.

According to process provided by the present invention, the components in said amorphous alloy can be present in a pure amorphous form, or in a form of a mixture of amorphous alloys and microcrystalline and/or crystalline alloys (i.e. a part of the alloy is in an amorphous form) wherein the microcrystalline and crystalline alloys are present in an total amount of preferably less than 30 wt. %. The presence of the amorphous alloy can be identified by the XRD method. A broad diffraction peak in the XRD spectrum means that the alloy is in a form of amorphous alloy. Preferably, the amorphous alloy is powder having a size less than or equal to 500 meshes.

According to process provided by the present invention, said catalyst further contains a matrix into which the amorphous alloy is dispersed. Preferably and based on the weight of the catalyst, the amount of the amorphous alloy is 20-90 wt. %, more preferably 20-60 wt. %, and the amount of the matrix is 10-80 wt. %, more preferably 40-80 wt. %.

According to process provided by the present invention, the matrix can be selected from those frequently used in catalysts in the art, e.g. one or more of non-oxidative porous inorganic oxides, molecular sieves, active carbons, clays, phosphates (e.g. aluminum phosphate), sulphates (e.g. magnesium sulphate), and metal halides (e.g $FeCl_3$, $SnCl_4$, $ZnCl_2$).

The non-oxidative porous inorganic oxides are well known to those skilled in the art, and can be one or more selected from alumina, silica, alumina-silica, zirconia, titania, zinc oxide, gallium oxide, boron oxide, and alkaline earth metal oxide. The non-oxidative porous inorganic oxides are commercially available, or can be prepared by a co-precipitation method which is well known to those skilled in the art.

Said molecular sieves are well known to those skilled in the art, e.g. silicon-aluminum molecular sieves, hetero-atom molecular sieves.

Said clays are well known to those skilled in the art, e.g. kaolin, halloysite, montmorillonite, diatomaceous earth, halloysite, saponite, rectorite, sepiolite, attapulgite, hydrotalcite, bentonite, more preferably kaolin, montmorillonite.

As known to those skilled in the art, a heteropolyacid, e.g. phosphotungstic acid and/or phosphomolybdic acid can be loaded on/in the matrix.

According to process provided by the present invention, preferably, said matrix contains an adjuvant which is loaded on/in the matrix and selected from one or more elements or oxides thereof of Group IA, IIA, IIIA, IVA, VA, IB, IIB, IVB, and VIII, and Lanthanide series of the Periodic Table of Elements. More preferably, said adjuvant is one or more elements or oxides thereof selected from Lanthanide series, and the third, fourth and fifth rows of Group IA, IIIA, IVA, VA, IB, IIB, IVB, VB, VIIB, VIIB, and VIII of the Periodic Table of Elements, even more preferably one or more elements or oxides selected from K, Ca, Mg, Ga, Sn, P, Cu, Zn, Zr, Fe, and La. Loading the adjuvant on/in the matrix can increase the activity and selectivity of the reaction.

According to process provided by the present invention, preferably and based on the weight of the matrix, the amount of the adjuvant is 0.5-40 wt. %.

The catalyst compounded from the amorphous alloy and matrix has a superior catalytic activity, selectivity of the target product, poisoning resistance, and repeatability of the catalyst property. Meanwhile, the stability of the catalyst is superior too. The regeneration period of the catalyst can be as long as 3 months or longer. Moreover, the catalyst is easily usable in the reaction. A reduction and activation step for a catalyst, which otherwise should be carried out prior to the reaction in the prior art and often is complex, difficult and time-consuming, can be omitted in the present process. The preparation method of the inventive catalyst is simple, easily operable, and easy to be scaled up in the industry.

Preferably, the catalyst can be prepared as follows:

(1) Preparing the Amorphous Alloy

The preparation method of the amorphous alloy comprises the steps of alloying a mixture of the first component Al and the second component in above mentioned amounts under vacuum and at a temperature above than their melting points, and rapidly quenching the alloyed mixture by a vacuum quench process, wherein the conditions for the rapid quench comprises a copper roller linear velocity of 20-40 m/s, an injection pressure of 0.05-0.1 MPa, and an injection temperature of 1100-2000° C. Then the resulting alloy is pulverized to a size of less than or equal to 500 meshes (i.e. more than or equal to 25 μm) to obtain the alloy powder.

(2) Preparing the Matrix

The above-mentioned adjuvant in an amount of 0.5-40 wt. % is loaded in/on the whole matrix or a part thereof by an ion exchange method, impregnation method or precipitation method well known to those skilled in the art.

In the ion exchange method, e.g. a matrix adhered with $H^+$ and/or $Na^+$ on the surface and an aqueous solution containing ions of the adjuvant element can be homogeneously mixed, heated to 80° C. and stirred for 1 hr, then filtered, and the filtration product is repeatedly washed with distilled water and dried at a temperature of 110° C.

In the impregnation method, e.g. a matrix can be impregnated in an aqueous solution containing ions of the adjuvant element at 60° C. for 8 hrs, dried at 110° C., and then calcined at 550° C. for 2 hrs.

In the precipitation method, e.g. a matrix and an aqueous solution containing ions of the adjuvant element can be mixed homogeneously, then a precipitation agent e.g. sodium carbonate is added to produce a precipitate, and the resultant precipitate is filtered, washed repeated with distilled water, dried at 110° C., and then calcined at 550° C. for 2 hrs.

(3) Compounding the Amorphous Alloy and the Matrix

As known to those skilled in the art, the amorphous alloy and the matrix can be compounded by a mechanical mixing method without any other component, or by adding an adhesive prior to the mechanical mixing. Said adhesive can be silica sol, alumina sol or mixture thereof.

The preparation method of the catalyst may comprise a step of alkaline-washing the amorphous alloy or the catalyst with an alkaline solution to extract a part of Al in the amorphous alloy. For example, the alkaline washing step can be carried out by contacting an alkaline solution e.g. sodium hydroxide in a concentration of 10-25 wt. % with the amorphous alloy powder or the catalyst obtained from the compounding of the amorphous alloy and the matrix, to extract a part of Al in the amorphous alloy. The conditions for the alkaline wash, e.g. time, temperature, concentration of the alkaline, can depend on the composition of the amorphous alloy or catalyst and the reaction process in which the catalyst is used. Preferably, the aluminum amount in the alloy after the alkaline washing step is no less than 0.5 wt. %, more preferably no less than 5 wt. %, but no more than 60 wt. %, more preferably no more than 55 wt. %, still more preferably no more than 20 wt. %, even preferably no more than 15 wt. %, based on the weight of the alloy. The contact temperature is from 0 to 50° C., and the contact time is from 0.5 to 5 hrs. Relative to the stoichiometry of the Al amount in the alloy, the alkaline, e.g. sodium carbonate, is suitably used in an excess of from 10 to 30 wt. %. The preferred step of extracting Al with an alkaline can increase the diffusion velocity of the reactants and thus increase the catalytic activity.

The composition of the catalyst is determined by the X-ray fluorescence spectroscopy (XRFS). The experimental instrument used is the X-ray fluorescence spectrometer 3271 type from Rigaku Industrial Corporation. A rhodium target, an excitation voltage of 50 kV, and an excitation current of 50 mA are employed in the experiment; the spectral line intensity of each element is detected by a scintillation counter and a proportional counter to perform a quantitative or semi-quantitative analysis.

According to process provided by the present invention, preferably, the conditions for converting the syngas into methanol, dimethyl ether, and low carbon olefins comprise a reaction temperature of 200-400° C., a reaction pressure of 0.5-6 MPa, a space velocity of the syngas feedstock of 1000-10000 mL/g·h, and a molar ratio between $H_2$ and CO in the syngas of from 1 to 3.

When the present process aims to obtain methanol and dimethyl ether as the main products, and the low carbon olefins as the byproducts, the reaction temperature is preferably 200-270° C. and the reaction pressure is preferably 1-6 MPa. When the present process aims to obtain the low carbon olefins as the main products, and methanol and dimethyl ether as the byproducts, the reaction temperature is preferably 270-400° C. and the reaction pressure is preferably 0.5-2 MPa.

The reactor can be a fluidized bed reactor or a fixed bed reactor, and the operation process can be carried out in batch mode or continuous mode.

The process according to the present invention preferably comprises a reduction step of the catalyst prior to contacting the catalyst with syngas. The reduction step comprises loading into the reactor the catalyst in an amount of from 1 to 5 grams, and prior to the reaction, purging the reactor containing the catalyst with a reductive gas at a purging temperature of 130-600° C. for 0.5-1 hr to active the catalyst. The reductive gas may be a mixture of hydrogen in an amount of 1-10 wt. % and inert gas which can be one or more gases selected from nitrogen, helium, and argon.

After the reduction step, the syngas feedstock in a space velocity of 1000-10000 mL/g·h is fed into the reactor at a reaction temperature of 200-400° C. and an operation pressure of 0.5-6 MPa. The syngas can be one or more gases which comprise $H_2$ and CO in a molar ratio of from 1 to 3, e.g. one or more gases selected from coke oven gases, liquefied gases, water gases, semi-water gases, natural gases, and oil field gases.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLE 1

1. Preparation of the Amorphous Alloy 20 g aluminum powder (industrial purity, the same below), 60 g copper powder (industrial purity, the same below) and 20 g ZnO (industrial purity, the same below) were mixed, then placed and heated in a vacuum button furnace under a vacuum degree of $10^{-2}$ Pa and at a temperature of 1200° C., the mixture was kept melting for 10 mins and then argon gas was fed into the furnace until the pressure in the furnace became atmospheric, and thus a mixture of melted Cu, Al, and ZnO was obtained.

The mixture of melted Cu, Al, and ZnO was rapidly quenched by a vacuum quench process to obtain a product of Al—Cu—ZnO alloy. The conditions for the rapid quench comprised a copper roller linear velocity of 30 m/s, an injection pressure of 0.08 MPa, and an injection temperature of 1300° C.

The obtained alloy product was pulverized under a ventilated environment to particles with a maximum size of 300 meshes (i.e. less than or equal to 48 μm). An X-ray powder diffractometer (D/MAX-2500 type X-ray diffractometer from Rigaku Cooperation, Cu Kα ray, a current of 100 mA, the same below) was used to analyze the obtained powder by XRD. The resultant XRD spectrum showed that only a broad diffuse peak at 2θ=42° was present (FIG. 1 (1)) which is the typical characteristic of an amorphous alloy. Therefore, the resultant Al—Cu—ZnO alloy product was an alloy in an amorphous form.

2. Preparing the Matrix of Mixed Oxides 112 g ZnO and 200 g distilled water were mixed, a mixed solution of 100 g aqueous solution of 63.32 wt. % ZrOCl$_2$ (analytic purity, Xinghua Songhe Chemical Reagent Factory, the same below), 50 g aqueous solution of 15 wt. % CaCl$_2$ (industrial purity) and 50 g aqueous solution of 1 wt. % HCl (analytic purity, Beijing Chemical Works) were added dropwise with vigorously stirring, then an aqueous solution of 5 wt. % sodium carbonate (analytic purity, Beijing Chemical Works, the same below) was added until the pH of the mixed liquid became 9. The resultant mixture was stirred for a further 1 hr after the addition was completed. The resultant precipitate was filtered, then washed repeatedly with distilled water until there was no Cl$^-$, dried at 110° C., and calcined at 550° C. for 2 hrs to obtain 160 g matrix containing 27.5 wt. % ZrO$_2$, 70 wt. % ZnO and 2.5 wt. % CaO adjuvant.

3. Preparing the Catalyst

The above amorphous alloy and matrix were mixed mechanically in a weight ratio of 2:3, tableted, pulverized and screened to particles having sizes of from 20 to 40 meshes. A catalyst was obtained which composition was shown in Table 1.

EXAMPLE 2

1. Preparation of the Amorphous Alloy

The preparation method of the amorphous alloy was similar to that described in Example 1. 55 g aluminum powder and 45 g copper powder were mixed, then placed and heated in a vacuum button furnace under a vacuum degree of $10^{-2}$ Pa and at a temperature of 1200° C., the mixture was kept melting for 10 mins and then argon gas was fed into the furnace until the pressure in the furnace became atmospheric, and thus a mixture of melted Cu and Al was obtained.

The mixture of melted Cu and Al was rapidly quenched by a vacuum quench process to obtain a product of Al—Cu alloy. The conditions for the rapid quench comprised a copper roller linear velocity of 30 m/s, an injection pressure of 0.08 MPa, and an injection temperature of 1300° C.

The obtained alloy product was pulverized under a ventilated environment to particles with a maximum size of 300 meshes (i.e. less than or equal to 48 μm). An X-ray powder diffractometer was used to analyze the obtained powder by XRD. The resultant XRD spectrum was similar to FIG. 1 (1) which is the typical characteristic of an amorphous alloy. Therefore, the resultant Al—Cu alloy product was an alloy in an amorphous form.

2. Preparing a Matrix Containing Active Carbon and Metal Chlorides 5 g FeCl$_3$ (analytic purity, Jiangyin Hengye Chemical Engineering Co. Ltd., China, the same below), 5 g SnCl$_4$ (analytic purity, Liaoyang Dingxin Chemical Engineering Co. Ltd., China), 30 g ZnCl$_2$ (industrial purity) and 60 g active carbon powders (Xinsen Tanye Co. Ltd., Shaowu city, Fujian Province, China) were sufficiently kneaded to give 100 g of matrix containing FeCl$_3$ 5 wt. %, SnCl$_4$ 5 wt. %, ZnCl$_2$ 30 wt. %, and active carbon 60 wt. %.

3. Preparing the Catalyst 33 g amorphous alloy, 100 g matrix, 12.5 g silica sol (40 wt. %, Sinopec Catalyst Company Qilu filiale) and 25 g alumina sol (20 wt. %, Sinopec Catalyst Company Qilu filiale) were mixed homogeneously, extruded from an extruder, pulverized and screened to particles having sizes of from 20 to 40 meshes, dried under a vacuum degree of $10^{-1}$ Pa and at a temperature of 120° C. for 4 hrs to obtain the catalyst which contained 23 wt. % of the amorphous alloy and its composition was shown in Table 1.

EXAMPLE 3

1. Preparation of the Amorphous Alloy 10 g P (industrial purity), 5 g La$_2$O$_3$ (analytic purity, Zibo Rongruida Micro Materials Plant, the same below) and 10 g ZnO were mixed homogeneously in a crucible and then compacted, 45 g melted copper powder was added into the crucible containing P, La$_2$O$_3$ and ZnO and cooled, and 30 g aluminum powder was added therein and mixed. The resultant mixture was placed in a vacuum button furnace under a vacuum degree of $10^{-2}$ Pa and at a temperature of 1200° C., the mixture was kept melting for 10 mins and then argon gas was fed into the furnace until the pressure in the furnace became atmospheric, and thus a melted mixture was obtained.

The melted mixture was rapidly quenched by a vacuum quench process to obtain a product of Al—Cu—P—$La_2O_3$—ZnO alloy. The conditions for the rapid quench comprised a copper roller linear velocity of 30 m/s, an injection pressure of 0.08 MPa, and an injection temperature of 1300° C.

The obtained alloy product was pulverized under a ventilated environment to particles with a maximum size of 300 meshes. An X-ray powder diffractometer was used to analyze the obtained powder by XRD. The resultant XRD spectrum showed that only a broad diffuse peak at 2θ=42° was present (the resultant XRD spectrum was similar to FIG. 1 (1)) which is the typical characteristic of an amorphous alloy. Therefore, the resultant Cu—Al—P—$La_2O_3$—ZnO alloy product was an alloy in an amorphous form.

2. Preparation of ZSM-5 Molecular Sieve Matrix 233 g ZSM-5 molecular sieve (a pilot sample from Sinopec Catalyst Company Jianchang filiale, MFI structure: $Na_2O$<0.2 wt. %, Si/Al ratio=40) and 3000 g 0.1 mol/L KOH (analytic purity, Beijing Chemical Works, the same below) were mixed, heated to 80° C. and stirred for 1 hr, the resultant precipitate was filtered and repeatedly washed by distilled water until the filtrate became neutral, dried at 110° C., and then calcined at 550° C. for 2 hrs to obtain 234 g of matrix containing ZSM-5 molecular sieve 99.5 wt. % and $K_2O$ adjuvant 0.5 wt. %.

3. Preparation of the Catalyst

The above amorphous alloy and matrix were mixed mechanically in a weight ratio of 3:7, tableted, pulverized and screened to particles having sizes of from 20 to 40 meshes. A catalyst was obtained which composition was shown in Table 1.

EXAMPLE 4

1. Preparation of the Amorphous Alloy 40 g aluminum powder, 10 g $Ga_2O_3$ and 50 g copper powder were mixed and then placed in a vacuum button furnace under a vacuum degree of $10^{-2}$ Pa and at a temperature of 1200° C., the mixture was kept melting for 10 mins and then argon gas was fed into the furnace until the pressure in the furnace became atmospheric, and thus a melted mixture was obtained.

The melted mixture was rapidly quenched by a vacuum quench process to obtain a product of Al—Cu—$Ga_2O_3$ alloy. The conditions for the rapid quench comprised a copper roller linear velocity of 30 m/s, an injection pressure of 0.08 MPa, and an injection temperature of 1300° C.

The obtained alloy product was pulverized under a ventilated environment to particles with a maximum size of 300 meshes. An X-ray powder diffractometer was used to analyze the obtained powder by XRD. The resultant XRD spectrum showed that only a broad diffuse peak at 2θ=42° was present (the resultant XRD spectrum was similar to FIG. 1 (1)) which is the typical characteristic of an amorphous alloy. Therefore, the resultant Al—Cu—$Ga_2O_3$ alloy product was an alloy in an amorphous form.

2. Preparation of γ-$Al_2O_3$ Matrix with an Adjuvant 86 g γ-$Al_2O_3$ (a sample from Sinopec Catalyst Company Jianchang filiale, the same below) and 40 g aqueous solution of 52.5 wt. % $Zn(NO_3)_2$ (analytic purity, Beijing Chemical Works, the same below) were mixed to impregnate $Zn(NO_3)_2$ on γ-$Al_2O_3$, heated to 60° C. for 8 hr aging, dried at 110° C., and then calcined at 550° C. for 2 hrs to obtain γ-$Al_2O_3$ loaded with ZnO.

5 g $La(NO_3)_3$ was formulated to 23 g 22 wt. % solution and impregnated on γ-$Al_2O_3$ loaded with ZnO, heated to 60° C. for 8 hr aging, dried at 110° C., and then calcined at 550° C. for 2 hrs to obtain γ-$Al_2O_3$ matrix with the adjuvant. The matrix contained 86 wt. % γ-$Al_2O_3$, 9 wt. % ZnO adjuvant, and 5 wt. % $La_2O_3$ adjuvant.

3. Preparation of the Catalyst

The above amorphous alloy and matrix were mixed mechanically in a weight ratio of 1:1, tableted, pulverized and screened to particles having sizes of from 20 to 40 meshes. A catalyst was obtained which composition was shown in Table 1.

EXAMPLE 5

1. Preparation of the Amorphous Alloy 30 g aluminum powder, 10 g ZnO, 10 g vanadium (industrial purity), 5 g Cr (industrial purity) and 45 g Cu were mixed and then placed in a vacuum button furnace under a vacuum degree of $10^{-2}$ Pa and at a temperature of 1900° C., the mixture was kept melting for 10 mins and then argon gas was fed into the furnace until the pressure in the furnace became atmospheric, and thus a melted mixture was obtained.

The melted mixture was rapidly quenched by a vacuum quench process to obtain a product of Al—Cu—V—Cr—ZnO alloy. The conditions for the rapid quench comprised a copper roller linear velocity of 30 m/s, an injection pressure of 0.08 MPa, and an injection temperature of 1500° C.

The obtained alloy product was pulverized under a ventilated environment to particles with a maximum size of 300 meshes. An X-ray powder diffractometer was used to analyze the obtained powder by XRD. The resultant XRD spectrum showed that only a broad diffuse peak at 2θ=42° was present (the resultant XRD spectrum was similar to FIG. 1 (1)) which is the typical characteristic of an amorphous alloy. Therefore, the resultant Al—Cu—V—Cr—ZnO alloy product was an alloy in an amorphous form.

2. Preparation of Matrix Containing Magnesium Sulfate and Silica 40 g magnesium sulfate (analytic purity, Beijing Wuzhou Shiji Hongxing Chemical Works), 10 g $FeCl_3$, 11.8 g 85 wt. % phosphoric acid (analytic purity, Beijing Chemical Works) and 40 g silica (Wuxi Jindinglonghua Chemical Co., LTD, the same below) were sufficiently mixed and vacuum dried at 120° C. for 4 hrs to obtain 100 g matrix.

3. Preparation of the Catalyst

The above amorphous alloy and matrix were mixed mechanically in a weight ratio of 3:2, tableted, pulverized and screened to particles having sizes of from 20 to 40 meshes. A catalyst was obtained which composition was shown in Table 1.

EXAMPLE 6

1. Preparation of the Amorphous Alloy 13 g active carbon powder, 15 g $MnO_2$ (industrial purity) and 2 g $SiO_2$ were mixed homogenously, 5 g potassium (industrial purity), 20 g aluminum and 45 g Cu were rapidly added therein. After a rapid mixing, the mixture was placed in a vacuum button furnace under a vacuum degree of $10^{-2}$ Pa and at a temperature of 1200° C., the mixture was kept melting for 10 mins and then argon gas was fed into the furnace until the pressure in the furnace became atmospheric, and thus a melted mixture was obtained.

The melted mixture was rapidly quenched by a vacuum quench process to obtain a product of Al—Cu—K—C—$MnO_2$—$SiO_2$ alloy. The conditions for the rapid quench comprised a copper roller linear velocity of 30 m/s, an injection pressure of 0.08 MPa, and an injection temperature of 1500° C.

The obtained alloy product was pulverized under a ventilated environment to particles with a maximum size of 300 meshes. An X-ray powder diffractometer was used to analyze the obtained powder by XRD. The resultant XRD spectrum showed that only a broad diffuse peak at $2\theta=42°$ was present (the resultant XRD spectrum was similar to FIG. 1 (1)) which is the typical characteristic of an amorphous alloy. Therefore, the resultant Al—Cu—K—C—$MnO_2$—$SiO_2$ alloy product was an alloy in an amorphous form.

2. Preparation of the Catalyst

The amorphous alloy and SAPO-34 molecular sieve (a pilot sample from Sinopec Catalyst Company Jianchang filiale, CHA structure: $Na_2O<0.2$ wt. %, Si/Al ratio=13) matrix were mixed mechanically in a weight ratio of 7:3, tableted, pulverized and screened to particles having sizes of from 20 to 40 meshes. A catalyst was obtained which composition was shown in Table 1.

EXAMPLE 7

1. Preparation of the Amorphous Alloy

The preparation method was similar to Example 6. The resulting XRD spectrum is similar to FIG. 1(1).

2. Preparation of the Compounded Catalyst

The amorphous alloy and active carbon powder matrix were mixed mechanically in a weight ratio of 9:1, tableted, pulverized and screened to particles having sizes of from 20 to 40 meshes. A catalyst was obtained which composition was shown in Table 1.

EXAMPLE 8

1. Preparation of the Amorphous Alloy 20 g $MnO_2$ and 5 g $ZrO_2$ were mixed homogeneously in a crucible and then compacted, 5 g melted Ni (industrial purity) was added into the crucible and cooled, and then 50 g Fe (industrial purity, the same below) and 20 g Al were added therein and mixed. The resultant mixture was placed in a vacuum button furnace under a vacuum degree of $10^{-2}$ Pa and at a temperature of 1200° C., the mixture was kept melting for 10 mins and then argon gas was fed into the furnace until the pressure in the furnace became atmospheric, and thus a melted mixture was obtained.

The melted mixture was rapidly quenched by a vacuum quench process to obtain a product of Al—Ni—Fe—$MnO_2$—$ZrO_2$ alloy. The conditions for the rapid quench comprised a copper roller linear velocity of 30 m/s, an injection pressure of 0.08 MPa, and an injection temperature of 1300° C.

Figure 2:
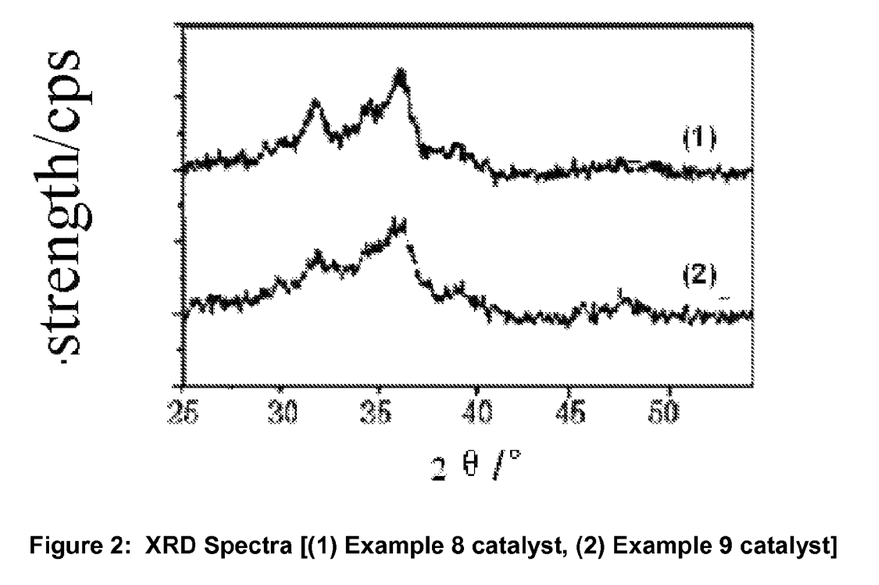

The obtained alloy product was pulverized under a ventilated environment to particles with a maximum size of 300 meshes. An X-ray powder diffractometer was used to analyze the obtained powder by XRD. The resultant XRD spectrum showed that only a broad diffuse peak was present (FIG. 2 (1)) which is the typical characteristic of an amorphous alloy. Therefore, the resultant Ni—Fe—Al—$MnO_2$—$ZrO_2$ alloy product was an alloy in an amorphous form.

2. Preparation of the Catalyst

The above amorphous alloy and clay (Jiangsu Xuyi Yuzhi Clay Plant) were mixed mechanically in a weight ratio of 1:1, tableted, pulverized and screened to particles having sizes of from 20 to 40 meshes. A catalyst was obtained which composition was shown in Table 1.

EXAMPLE 9

1. Preparation of the Amorphous Alloy 20 g $ZrO_2$ was placed in a crucible, and then 40 g molybdenum (industrial purity) and 40 g Al were added therein and mixed. The resultant mixture was placed in a vacuum button furnace under a vacuum degree of $10^{-2}$ Pa and at a temperature of 1200° C., the mixture was kept melting for 10 mins and then argon gas was fed into the furnace until the pressure in the furnace became atmospheric, and thus a melted mixture was obtained.

The melted mixture was rapidly quenched by a vacuum quench process to obtain a product of Al—Mo—$ZrO_2$ alloy. The conditions for the rapid quench comprised a copper roller linear velocity of 30 m/s, an injection pressure of 0.08 MPa, and an injection temperature of 1300° C.

The obtained alloy product was pulverized under a ventilated environment to particles with a maximum size of 300 meshes. An X-ray powder diffractometer was used to analyze the obtained powder by XRD. The resultant XRD spectrum showed that only a broad diffuse peak was present (FIG. 2(2)) which is the typical characteristic of an amorphous alloy. Therefore, the resultant Mo—Al—$ZrO_2$ alloy product was an alloy in an amorphous form.

2. Preparation of the Matrix Loaded with a Heteropolyacid 70 g $SiO_2$ was impregnated with 40 g aqueous solution of 62.5 wt. % $Cu(NO_3)_2$ (analytic purity, Zibo Rongruida Micro Materials Plant), dried at 80° C. for 6 hrs, 120° C. for 4 hrs, and then calcined at 550° C. for 2 hrs to obtain a CuO—$SiO_2$ complex.

The CuO—$SiO_2$ complex was impregnated with 40 g aqueous solution of 12.5 wt. % $Ga(NO_3)_3$ (analytic purity, Hunan Huaihua Yinhuan Smelt Co., Ltd.), then dried at 80° C. for 6 hrs, 120° C. for 4 hrs, and then calcined at 550° C. for 2 hrs to obtain a $Ga_2O_3$—CuO—$SiO_2$ complex.

Finally, the $Ga_2O_3$—CuO—$SiO_2$ complex was impregnated with 32 g 50 wt. % phosphotungstic acid (HPW) (analytic purity, Kunshan Xingbang W&M Technology Co., Ltd.) as heteropolyacid, dried at 80° C. for 6 hrs, 120° C. for further 4 hrs, and then calcined at 550° C. for 2 hrs to obtain a matrix containing the loaded heteropolyacid and adjuvant, wherein the amount of the phosphotungstic acid as heteropolyacid was 15.8 wt. %, the amount of adjuvant $Ga_2O_3$ was 3.7 wt. %, and the amount of adjuvant CuO was 10.5 wt. %.

3. Preparation of the Catalyst

The above amorphous alloy and matrix were mixed mechanically in a weight ratio of 3:2, tableted, pulverized and screened to particles having sizes of from 20 to 40 meshes. A catalyst was obtained which composition was shown in Table 1.

EXAMPLE 10

1. Preparation of the Amorphous Alloy 5 g ZnO, 15 g CoO (industrial purity) and 16 g copper powder were mixed homogeneously, and then 20 g Al and 30 g Fe were added therein. After a rapid mixing, the mixture was placed in a vacuum button furnace under a vacuum degree of $10^{-2}$ Pa and at a temperature of 1200° C., the mixture was kept melting for 10 mins and then argon gas was fed into the furnace until the pressure in the furnace became atmospheric, and thus a melted mixture was obtained.

The melted mixture was rapidly quenched by a vacuum quench process to obtain a product of Al—Fe—ZnO—CoO—Cu alloy. The conditions for the rapid quench comprised a copper roller linear velocity of 30 m/s, an injection pressure of 0.08 MPa, and an injection temperature of 1300° C.

The obtained alloy product was pulverized under a ventilated environment to particles with a maximum size of 300 meshes. An X-ray powder diffractometer was used to analyze the obtained powder by XRD. The resultant XRD spectrum showed that only a broad diffuse peak was present (the resultant XRD spectrum was similar to FIG. 1 (1)) which is the typical characteristic of an amorphous alloy. Therefore, the resultant Al—Fe—ZnO—CoO—Cu alloy product was an alloy in an amorphous form.

2. Preparation of the aluminum phosphate matrix

10% $Al(NO_3)_3$ and 10 wt. % phosphate solution were mixed in a Al/P molar ratio of 3:1, then 4N ammonia water (analytic purity, Beijing Chemical Works) was slowly added into the mixed solution until the pH became 9, the resultant mixture was filtered by suction, washed with ethanol for three times, dried under vacuum at 120° C. for 4 hrs, and then calcined at 650° C. for 3 hrs to obtain 100 g aluminum phosphate matrix.

3. Preparation of the Catalyst

The above amorphous alloy and matrix were mixed mechanically in a weight ratio of 2:3, tableted, pulverized and screened to particles having sizes of from 20 to 40 meshes. A catalyst was obtained which composition was shown in Table 1.

EXAMPLE 11

1. Preparation of the Catalyst Containing an Amorphous Alloy and an Oxide Matrix The preparation method was same to Example 1.

2. Alkaline-Washing Step for the Amorphous Alloy 100 g the above mentioned catalyst particles containing the amorphous alloy and the oxide matrix and having a size of 20-40 meshes were contacted with 400 g solution of 10 wt. % sodium hydroxide to carry out the alkaline washing step to extract a part of Al in the amorphous alloy. The contacting temperature was 5° C., and the contacting time was 0.5 hr. The catalyst was filtered after the reaction finished, and washed repeatedly with distilled water until the pH of the washing water became 7. XRFS results showed that the Al:Cu ratio by weight in the catalyst was 0.23. From the ratio, the amount of Al in the amorphous alloy following the alkaline washing step was calculated to be 15 wt. %, based on the weight of the alloy. The catalyst was stored in anhydrous ethanol for further use.

EXAMPLE 12

1. Preparation of the Catalyst Containing an Amorphous Alloy and an Oxide Matrix The preparation method was same to Example 1.

2. Alkaline-Washing Step for the Amorphous Alloy 100 g the above mentioned catalyst particles containing the amorphous alloy and the oxide matrix and having a size of 20-40 meshes were contacted with 230 g solution of 20 wt. % sodium hydroxide to carry out the alkaline washing step to extract a part of Al in the amorphous alloy. The contacting temperature was 20° C., and the contacting time was 1.0 hr. The catalyst was filtered after the reaction finished, and washed repeatedly with distilled water until the pH of the washing water became 7. XRFS results showed that the Al:Cu ratio by weight in the catalyst was 0.07. From the ratio, the amount of Al in the amorphous alloy following the alkaline washing step was calculated to be 5 wt. %, based on the weight of the alloy. The catalyst was stored in anhydrous ethanol for further use.

EXAMPLE 13

1. Preparation of the Catalyst Containing an Amorphous Alloy and an Oxide Matrix The preparation method was same to Example 1.

2. Alkaline-Washing Step for the Amorphous Alloy 100 g the above mentioned catalyst particles containing the amorphous alloy and the oxide matrix and having a size of 20-40 meshes were contacted with 300 g solution of 15 wt. % sodium hydroxide to carry out the alkaline washing step to extract a part of Al in the amorphous alloy. The contacting temperature was 50° C., and the contacting time was 5 hrs. The catalyst was filtered after the reaction finished, and washed repeatedly with distilled water until the pH of the washing water became 7. XRFS results showed that the Al:Cu ratio by weight in the catalyst was 0.0067. From the ratio, the amount of Al in the amorphous alloy following the alkaline washing step was calculated to be 0.5 wt. %, based on the weight of the alloy. The catalyst was stored in anhydrous ethanol for further use.

TABLE 1

| Example No. | Composition of the amorphous alloy(wt.) | Matrix composition (wt.) | The method of introduction of the adjuvant | wt. % of the amorphous alloy in the catalyst |
|---|---|---|---|---|
| 1 | Al (20%), Cu (60%), ZnO(20%) | ZnO(70%), ZrO$_2$(27.5%) CaO(2.5%) | Precipitation | 40% |
| 2 | Al (55%), Cu (45%) | FeCl$_3$(5%), SnCl$_4$(5%), ZnCl$_2$(30%), active carbon(60%) | No | 23% |
| 3 | Al (30%), Cu (45%), ZnO (10%), La2O3 (5%), P(10%) | ZSM-5 molecular sieve (99.5%), K2O(0.5%) | Ion exchange | 30% |
| 4 | Al (40%), Cu (50%), Ga2O3 (10%) | γ-Al2O3(86%), ZnO (9%), La2O3(5%) | Impregnation | 50% |
| 5 | Al (30%), Cu (45%), ZnO(10%), V(10%), Cr(5%) | magnesium sulfate(40%), silica(40%), phosphoric acid(10%), FeCl3(10%) | No | 60% |
| 6 | Al (20%), Cu (45%), C(13%), K(5%), MnO2(15%), SiO2(2%) | Heteroatom molecular sieve | No | 70% |
| 7 | Same to example 6 | Active carbon | No | 90% |
| 8 | Al (20%), Fe(50%), MnO2(20%), Ni(5%), ZrO2(5%) | Clay | No | 50% |
| 9 | Al (40%), Mo(40%), ZrO2 (20%) | SiO2(70%), phosphotungstic acid (15.8%), CuO(10.5%), Ga2O3(3.7%) | Precipitation | 60% |
| 10 | Al (20%), Fe(30%), Cu(16%), ZnO(5%), CoO(15%) | Aluminum phosphate | No | 40% |
| 11 | Al (15%), Cu (63.7%), ZnO(21.3%) | ZnO(70%), ZrO2(27.5%) CaO(2.5%) | Precipitation | 38.5% |
| 12 | Al (5%), Cu (71.3%), ZnO(23.7%) | ZnO(70%), ZrO2(27.5%) CaO(2.5%) | Precipitation | 35.95% |
| 13 | Al (0.5%), Cu (74.6%), ZnO(24.9%) | ZnO(70%), ZrO2(27.5%) CaO(2.5%) | Precipitation | 34.9% |

Comparative Example 1

Figure 1:
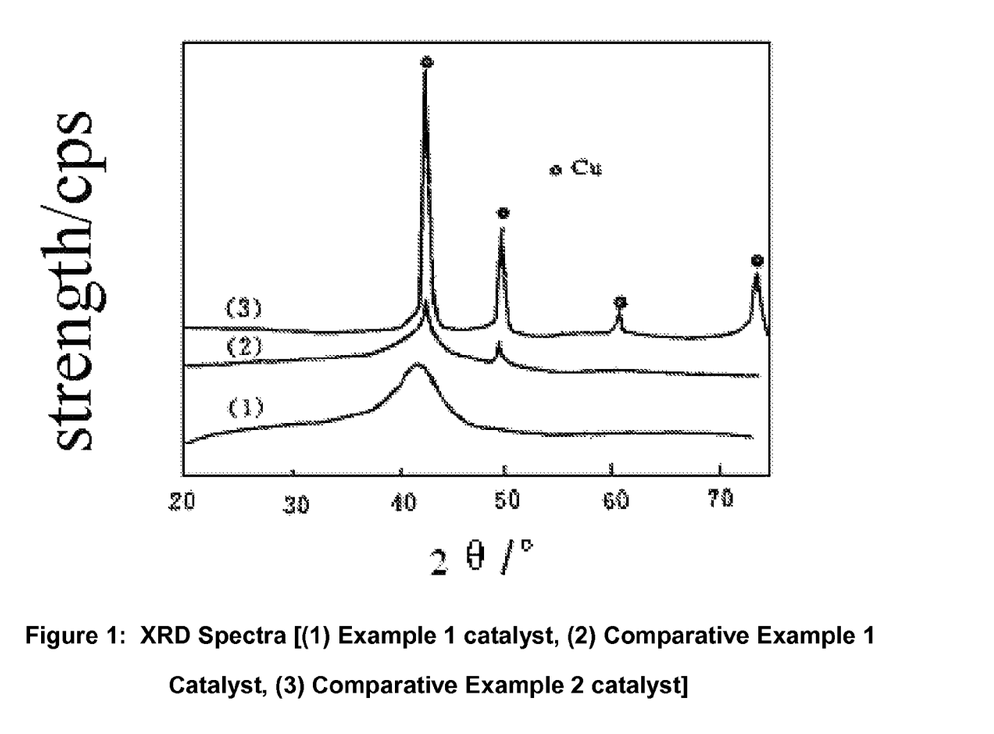
FIGS. 1-3 are the XRD spectrum of the alloys prepared by the inventive Examples and Comparative Examples.

40 g γ-Al$_2$O$_3$ calcined at 550° C. for 4 hrs which was used as the component for methanol dehydration reaction, and 20 g commercial methanol synthesis catalyst QC308 (Nanjing Qingshan Chemical Engineering Co., Ltd., a crystalline alloy wherein Al had been removed by alkaline washing and contained Cu and Zn, and its XRD spectrum was shown in FIG. 1 (2)) which was used as the component for methanol synthesis reaction were mechanically mixed, tableted, pulverized, and screened to particles having sizes of 20-40 meshes. The comparative catalyst was obtained wherein the weight ratio between the component for methanol dehydration reaction and the component for methanol synthesis reaction was 2:1.

Comparative Example 2

1. Preparation of the Crystalline Alloy 20 g aluminum powder (industrial purity, the same below), 60 g copper powder (industrial purity, the same below) and 20 g ZnO (industrial purity, the same below) were mixed, then placed and heated in a vacuum button furnace under a vacuum degree of $10^{-2}$ Pa and at a temperature of 1200° C., the mixture was kept melting for 10 mins and then argon gas was fed into the furnace until the pressure in the furnace became atmospheric, and thus a mixture of melted Cu, Al, and ZnO was obtained.

The mixture of melted Cu, Al, and ZnO was rapidly quenched by a vacuum quench process to obtain a product of Al—Cu—ZnO alloy. The conditions for the rapid quench comprised a copper roller linear velocity of 10 m/s, an injection pressure of 0.08 MPa, and an injection temperature of 1100° C. The resultant Al—Cu—ZnO alloy was calcined under N$_2$ protective atmosphere at 600° C. for 4 hrs to obtain crystalline alloy powders.

An X-ray powder diffractometer (D/MAX-2500 type X-ray diffractometer from Rigaku Cooperation, Cu Kα ray, a current of 100 mA, the same below) was used to analyze the obtained powder by XRD. The resultant XRD spectrum showed that a sharp peak at 2θ=42° was present (FIG. 1 (3)). Therefore, the resultant Al—Cu—ZnO alloy product was an alloy in a crystalline form.

2. Preparing the Matrix of Mixed Oxides 112 g ZnO and 200 g distilled water were mixed, a mixed solution of 100 g aqueous solution of 63.32 wt. % ZrOCl$_2$ (analytic purity, Xinghua Songhe Chemical Reagent Factory, the same below), 50 g aqueous solution of 15 wt. % CaCl$_2$ (industrial purity) and 50 g aqueous solution of 1 wt. % HCl (analytic purity, Beijing Chemical Works) were added dropwise with vigorously stirring, then an aqueous solution of 5 wt. % sodium carbonate (analytic purity, Beijing Chemical Works, the same below) was added until the pH of the mixed liquid became 9. The resultant mixture was stirred for a further 1 hr after the addition was completed. The resultant precipitate was filtered, then washed repeatedly with distilled water until there was no Cl$^-$, dried at 110° C., and calcined at 550° C. for 2 hrs to obtain 160 g matrix containing 27.5 wt. % ZrO$_2$, 70 wt. % ZnO and 2.5 wt. % CaO adjuvant.

3. Preparing the Catalyst

The above crystalline alloy and matrix were mixed mechanically in a weight ratio of 2:3, tableted, pulverized and screened to particles having sizes of from 20 to 40 meshes.

Comparative Example 3

1. Preparation of the Amorphous Alloy 73.3 g copper powder (industrial purity, the same below) and 26.7 g ZnO (industrial purity, the same below) were mixed, then placed and heated in a vacuum button furnace under a vacuum degree of $10^{-2}$ Pa and at a temperature of 1200° C., the mixture was kept melting for 10 mins and then argon gas was fed into the furnace until the pressure in the furnace became atmospheric, and thus a mixture of melted Cu and ZnO was obtained.

The mixture of melted Cu and ZnO was rapidly quenched by a vacuum quench process to obtain a product of Cu—ZnO alloy. The conditions for the rapid quench comprised a copper roller linear velocity of 30 m/s, an injection pressure of 0.08 MPa, and an injection temperature of 1300° C.

The obtained alloy product was pulverized under a ventilated environment to particles with a maximum size of 300 meshes (i.e. less than or equal to 48 μm). An X-ray powder diffractometer (D/MAX-2500 type X-ray diffractometer from Rigaku Cooperation, Cu Kα ray, a current of 100 mA, the same below) was used to analyze the obtained powder by XRD. The resultant XRD spectrum was similar to FIG. 1 (1) which is the typical characteristic of an amorphous alloy. Therefore, the resultant Cu—ZnO alloy product was an alloy in an amorphous form.

2. Preparing the Matrix of Mixed Oxides 112 g ZnO and 200 g distilled water were mixed, a mixed solution of 100 g aqueous solution of 63.32 wt. % $ZrOCl_2$ (analytic purity, Xinghua Songhe Chemical Reagent Factory, the same below), 50 g aqueous solution of 15 wt. % $CaCl_2$ (industrial purity) and 50 g aqueous solution of 1 wt. % HCl (analytic purity, Beijing Chemical Works) were added dropwise with vigorously stirring, then an aqueous solution of 5 wt. % sodium carbonate (analytic purity, Beijing Chemical Works, the same below) was added until the pH of the mixed liquid became 9. The resultant mixture was stirred for a further 1 hr after the addition was completed. The resultant precipitate was filtered, then washed repeatedly with distilled water until there was no $Cl^-$, dried at 110° C., and calcined at 550° C. for 2 hrs to obtain 160 g matrix containing 27.5 wt. % $ZrO_2$, 70 wt. % ZnO and 2.5 wt. % CaO adjuvant.

3. Preparing the Catalyst

The above amorphous alloy and matrix were mixed mechanically in a weight ratio of 2:3, tableted, pulverized and screened to particles having sizes of from 20 to 40 meshes.

Comparative Example 4

The comparative catalyst was prepared by the following method:

70 g $SiO_2$ was impregnated with 40 g aqueous solution of 62.5 wt. % $Cu(NO_3)_2$ (analytic purity, Zibo Rongruida Micro Materials Plant), then dried at 80° C. for 6 hrs, 120° C. for 4 hrs, then calcined at 550° C. for 2 hrs to obtain $CuO$—$SiO_2$ complex.

Figure 3:
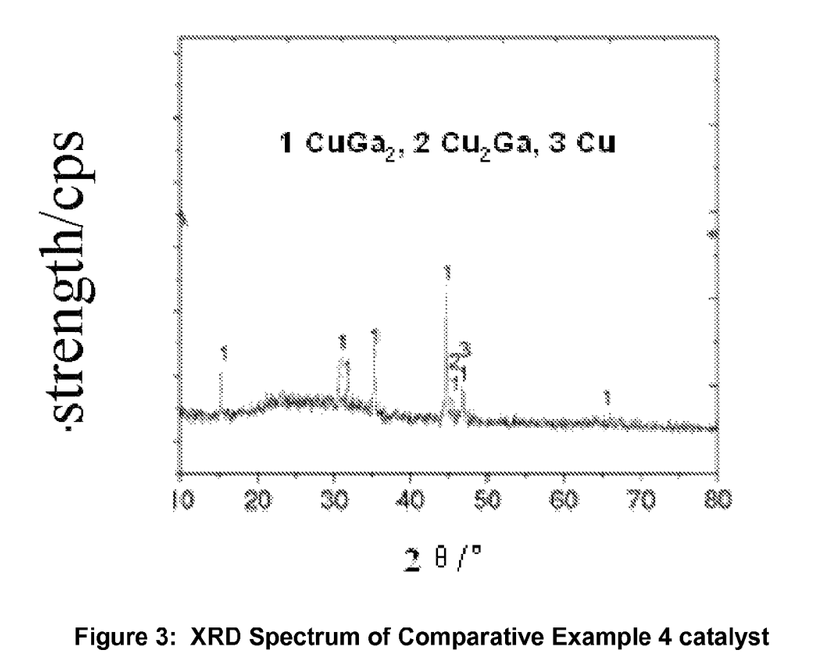

The resultant $CuO$—$SiO_2$ complex was further impregnated with 40 g aqueous solution of 12.5 wt. % $Ga(NO_3)_3$ (analytic purity, Hunan Huaihua Yinhuan Smelt Co., Ltd.), then dried at 80° C. for 6 hrs, 120° C. for 4 hrs, and then calcined at 550° C. for 2 hrs to obtain $Ga_2O_3$—$CuO$—$SiO_2$ complex (FIG. 3).

Finally, the $Ga_2O_3$—$CuO$—$SiO_2$ complex was impregnated with 32 g 50 wt. % phosphotungstic acid (HPW) (analytic purity, Kunshan Xingbang W&M Technology Co., Ltd.) as heteropolyacid, dried at 80° C. for 6 hrs, 120° C. for further 4 hrs, and then calcined at 550° C. for 2 hrs to obtain a matrix containing the loaded heteropolyacid and adjuvant, wherein the amount of the phosphotungstic acid as heteropolyacid was 15.8 wt. %, the amount of adjuvant $Ga_2O_3$ was 3.7 wt. %, and the amount of adjuvant CuO was 10.5 wt. %.

EXAMPLE 14

The process for preparing methanol, dimethyl ether, and low carbon olefins from syngas was carried out by means of each catalyst prepared from Examples 1-13 and Comparative Examples 1-4.

The gas phase reaction was carried out in a pressurized reaction evaluation apparatus of continuous flow fixed bed reactor.

1.5 g of catalyst was loaded into the reactor. Prior to the reaction, the reactor containing the catalyst was purged with a reductive gas for 0.5 hr. Subsequently, the reaction temperature was adjusted, and syngas was fed into the reactor in a feed space velocity. The composition of the reductive gas, purge temperature, operation conditions and composition of the feedstock syngas were listed in Table 2. A sample was taken for analysis after the reaction proceeded for 3 hrs. Carbon monoxide was on line analyzed by HP 6890 type gas chromatograph, and the products of methanol, dimethyl ether and low carbon olefins were analyzed by PORAPAK-N chromatographic column.

In order to compare Example 1 with Comparative Examples 1-3, and Example 7 with Comparative Example 4, Example 1 and Comparative Examples 1-3 shared the substantially same operation conditions and feedstock syngas composition, and Example 7 and Comparative Example 4 shared too.

TABLE 2

| Catalyst No. | Composition of the reductive gas (wt. %) | Purge temperature/° C. | Feed space velocity/ mL/g · h | Reaction pressure/ MPa | Reaction temperature/° C. | Composition of the feedstock gas (wt. %) |
|---|---|---|---|---|---|---|
| Example 1 | 5% $H_2$, 95% $N_2$ | 130 | 1000 | 4 | 230 | 31% CO, 6% $CO_2$, 63% $H_2$ |
| Comparative Example 1 | 5% $H_2$, 95% $N_2$ | 130 | 1000 | 4 | 230 | 31% CO, 6% $CO_2$, 63% $H_2$ |

TABLE 2-continued

| Catalyst No. | Composition of the reductive gas (wt. %) | Purge temperature/° C. | Feed space velocity/ mL/g · h | Reaction pressure/ MPa | Reaction temperature/° C. | Composition of the feedstock gas (wt. %) |
|---|---|---|---|---|---|---|
| Comparative Example 2 | 5% $H_2$, 95% $N_2$ | 130 | 1000 | 4 | 230 | 31% CO, 6% $CO_2$, 63% $H_2$ |
| Comparative Example 3 | 5% $H_2$, 95% $N_2$ | 130 | 1000 | 4 | 230 | 31% CO, 6% $CO_2$, 63% $H_2$ |
| Example 2 | 1% $H_2$, 99% $N_2$ | 600 | 1500 | 4 | 250 | 31% CO, 6% $CO_2$, 63% $H_2$ |
| Example 3 | 5% $H_2$, 95% He | 300 | 1500 | 4 | 270 | 31% CO, 6% $CO_2$, 63% $H_2$ |
| Example 4 | 5% $H_2$, 95% $N_2$ | 240 | 1000 | 6 | 200 | 31% CO, 6% $CO_2$, 63% $H_2$ |
| Example 5 | 5% $H_2$, 95% Ar | 400 | 5000 | 4 | 270 | 42% CO, 8% $CO_2$, 50% $H_2$ |
| Example 6 | 5% $H_2$, 80% $N_2$, 15% Ar | 300 | 1500 | 1 | 290 | 42% CO, 8% $CO_2$, 50% $H_2$ |
| Example 7 | 10% $H_2$, 90% $N_2$ | 280 | 2700 | 2 | 270 | 26% CO, 2% $CO_2$, 72% $H_2$ |
| Comparative Example 4 | 10% $H_2$, 90% $N_2$ | 280 | 2700 | 2 | 270 | 26% CO, 2% $CO_2$, 72% $H_2$ |
| Example 8 | 5% $H_2$, 75% He, 20% $N_2$ | 400 | 9000 | 1 | 400 | 26% CO, 2% $CO_2$, 72% $H_2$ |
| Example 9 | 5% $H_2$, 95% $N_2$ | 300 | 1500 | 0.5 | 350 | 26% CO, 2% $CO_2$, 72% $H_2$ |
| Example 10 | 5% $H_2$, 95% $N_2$ | 400 | 1500 | 0.5 | 300 | 42% CO, 8% $CO_2$, 50% $H_2$ |
| Example 11 | 5% $H_2$, 95% $N_2$ | 130 | 1000 | 4 | 230 | 31% CO, 6% $CO_2$, 63% $H_2$ |
| Example 12 | 5% $H_2$, 95% $N_2$ | 130 | 1000 | 4 | 230 | 31% CO, 6% $CO_2$, 63% $H_2$ |
| Example 13 | 5% $H_2$, 95% $N_2$ | 130 | 1000 | 4 | 230 | 31% CO, 6% $CO_2$, 63% $H_2$ |

The CO conversion, selectivity of each of methanol, dimethyl ether, ethylene, and propylene, as well as carbon availability during the process for preparing methanol, dimethyl ether, and low carbon olefins from syngas were calculated by the following equations and the results were shown in Table 3.

CO conversion (%)=moles of CO consumed by the reaction/moles of CO fed into the reaction Dimethyl ether selectivity (%)=moles of dimethyl ether produced by the reaction/moles of CO consumed by the reaction Methanol selectivity (%)=moles of methanol produced by the reaction/moles of CO consumed by the reaction Ethylene selectivity (%)=(moles of ethylene produced by the reaction×2)/moles of CO consumed by the reaction Propylene selectivity (%)=(moles of propylene produced by the reaction×3)/moles of CO consumed by the reaction Carbon availability (%)=(moles of CO consumed by the reaction−moles of CO produced by the reaction)/moles of CO fed into the reaction.

TABLE 3

| Catalyst | CO conversion (%) | Dimethyl ether selectivity (%) | Methanol selectivity (%) | Ethylene selectivity (%) | Propylene selectivity (%) | Carbon availability (%) |
|---|---|---|---|---|---|---|
| Example 1 | 80 | 93 | 3 | 1.9 | 1.5 | 64 |
| Comparative Example 1 | 70 | 72 | 23 | 1.4 | 1 | 59 |
| Comparative Example 2 | 75 | 80 | 16 | 1.5 | 1.2 | 61 |
| Comparative Example 3 | 76 | 64 | 30 | 1.0 | 1.2 | 65 |
| Example 2 | 85 | 90 | 2 | 1.3 | 1.1 | 65 |
| Example 3 | 84 | 90 | 2 | 1.5 | 1.2 | 65 |
| Example 4 | 87 | 91 | 4 | 2.7 | 1.9 | 66 |
| Example 5 | 91 | 92 | 2 | 2.3 | 1.7 | 65 |
| Example 6 | 93 | 1 | — | 19 | 18 | 66 |
| Example 7 | 94 | 5 | — | 23 | 17 | 67 |
| Comparative Example 4 | 30 | 12 | 5 | 5 | 14 | 20 |
| Example 8 | 95 | 21 | 0.6 | 26 | 20 | 70 |
| Example 9 | 93 | 23 | — | 34 | 26 | 71 |
| Example 10 | 92 | 18 | 0.1 | 25 | 20 | 64 |

TABLE 3-continued

| Catalyst | CO conversion (%) | Dimethyl ether selectivity (%) | Methanol selectivity (%) | Ethylene selectivity (%) | Propylene selectivity (%) | Carbon availability (%) |
|---|---|---|---|---|---|---|
| Example 11 | 85 | 92 | 4 | 1.8 | 1.4 | 66 |
| Example 12 | 88 | 93 | 3 | 1.9 | 1.5 | 64 |
| Example 13 | 87 | 92 | 4.2 | 1.8 | 1.5 | 65 |

It can be seen from Table 3, in the process for preparing methanol, dimethyl ether, and low carbon olefins from syngas, the catalysts according to the present invention can achieve a high CO conversion, a high selectivity of the target product, and high carbon availability.

We claim:

1. A process for preparing methanol, dimethyl ether, and low carbon olefins from syngas, wherein the process comprises the step of contacting syngas with a catalyst under the conditions for converting the syngas into methanol, dimethyl ether, and low carbon olefins, characterized in that,
the catalyst contains an amorphous alloy consisting of a first component Al and a second component, said second component being one or more elements or oxides thereof selected from the third, fourth and fifth rows of Group IA, IIIA, IVA, VA, IB, IIB, IVB, VB, VIB, VIIB, and VIII, and Lanthanide series of the Periodic Table of Elements, and said second component being different from the first component Al,
wherein, based on the total weight of the amorphous alloy, the amount of Al is 0.5-60 wt. %, and the amount of the second component is 40-99.5 wt. %,
wherein said catalyst further comprises a matrix into which the amorphous alloy is dispersed said matrix contains an adjuvant loaded on/in the matrix.

2. The process according to claim 1, wherein based on the total weight of the amorphous alloy, the amount of Al is 20-55 wt. %, and the amount of the second component is 45-80 wt. %.

3. The process according to claim 1, wherein based on the total weight of the amorphous alloy, the amount of Al is 0.5-20 wt. %, and the amount of the second component is 80-99.5 wt. %.

4. The process according to claim 1, wherein said second component is one or more elements or oxides thereof selected from Cu, Zn, V, Cr, Mn, Fe, Co, Ni, K, Zr, Mo, Sn, C, Si, La, and P.

5. The process according to claim 1, wherein said second component comprises Cu or the oxide thereof.

6. The process according to claim 1, wherein said second component comprises Cu and Zn or the oxides thereof.

7. The process according to claim 1, wherein said second component consists of Cu and Zn or the oxides thereof.

8. The process according to claim 5, wherein the amount of the Group VIII element or the oxide thereof, if present, is less than 30 wt. %, based on the total weight of the amorphous alloy.

9. The process according to claim 1, wherein based on the total weight of the catalyst, the amount of the amorphous alloy is 20-90 wt. %, and the amount of the matrix is 10-80 wt. %.

10. The process according to claim 9, wherein said matrix is one or more substances selected from non-oxidative porous inorganic oxides, molecular sieves, active carbons, clays, phosphates, sulphates, and metal halides.

11. The process according to claim 9, wherein said matrix comprises materials selected from one or more elements or oxides thereof of Group IA, IIA, IIIA, IVA, VA, IB, IIB, IVB, and VIII, and Lanthanide series of the Periodic Table of Elements.

12. The process according to claim 11, wherein said adjuvant is one or more elements or oxides thereof selected from Lanthanide series, and the third, fourth and fifth rows of Group IA, IIIA, IVA, VA, IB, IIB, IVB, VB, VIB, VIIB, and VIII of the Periodic Table of Elements.

13. The process according to claim 11, wherein said adjuvant is one or more elements or oxides selected from K, Ca, Mg, Ga, Sn, P, Cu, Zn, Zr, Fe, and La.

14. The process according to claim 11, wherein, based on the weight of the matrix, the amount of the adjuvant is 0.5-40 wt. %.

15. The process according to claim 1, wherein the conditions for converting the syngas into methanol, dimethyl ether, and low carbon olefins comprise a reaction temperature of 200-400° C., a reaction pressure of 0.5-6 MPa, a space velocity of the syngas feed of 1000-10000 mL/g·h, and a molar ratio between H2 and CO in the syngas of from 1 to 3.

16. The process according to claim 15, wherein the reaction temperature is 200-270° C., and the reaction pressure is 1-6 MPa, whereas methanol and dimethyl ether are produced as the main products, and the low carbon olefins are produced as the byproducts.

17. The process according to claim 15, wherein the reaction temperature is 270-400° C., and the reaction pressure is 0.5-2 MPa, whereas the low carbon olefins are produced as the main products, and methanol and dimethyl ether are produced as the byproducts.

18. The process according to claim 1, wherein the amorphous alloy is prepared by a method comprising the following steps: alloying a mixture of the first component Al and the second component under vacuum and at a temperature above than their melting points, rapidly quenching the alloyed mixture by a vacuum quench process, and then pulverizing the resulting alloy.

19. The process according to claim 1, wherein the catalyst is prepared by a method comprising a step of alkaline-washing the amorphous alloy or the catalyst with an alkaline solution to extract a part of Al in the amorphous alloy.

20. The process according to claim 1, wherein the amorphous alloy is powder having a size of less than or equal to 500 meshes.

* * * * *